United States Patent [19]

Savina et al.

[11] Patent Number: 5,965,780
[45] Date of Patent: Oct. 12, 1999

[54] METHOD FOR EXTRACTING 2-PHENYLETHANOL

[75] Inventors: Jean-Pierre Savina, Brunoy; Danièle Kohler, Le Perreux; Pascal Brunerie, Santeny, all of France

[73] Assignee: Pernod Ricard, France

[21] Appl. No.: 08/904,010

[22] Filed: Jul. 31, 1997

[30] Foreign Application Priority Data

Aug. 1, 1996 [FR] France .................................. 96 09730

[51] Int. Cl.$^6$ .................................................. C07C 31/18
[52] U.S. Cl. ............................................ 568/715; 568/810
[58] Field of Search ..................................... 568/715, 810

[56] References Cited

FOREIGN PATENT DOCUMENTS 59062504  4/1984  Japan .

OTHER PUBLICATIONS

Database WPI, section ch, week 8004, Derwent Publications Ltd., London, GB, Class B05, AN 80–06919c.

*Primary Examiner*—Michael L. Shippen
*Attorney, Agent, or Firm*—Blakely, Sokoloff, Taylor & Zafman

[57] ABSTRACT

The invention relates to a method for extracting 2-phenylethanol, in which the 2-phenylethanol is extracted from the distillation residues obtained during the production of alcohol.

8 Claims, No Drawings

METHOD FOR EXTRACTING 2-PHENYLETHANOL

The invention relates to a method for extracting 2-phenylethanol.

2-Phenylethanol, whose structural formula is given below, is an aromatic compound which, when purified, gives off a pleasant odour of roses and, in this respect, is very widely used in the agrifood, cosmetics and perfumery industries.

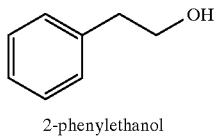

2-phenylethanol

Natural 2-phenylethanol may be obtained by distillation of rose petals, which requires a relatively large set-up to cultivate roses specifically for this purpose, and is inevitably reflected in the cost of natural 2-phenylethanol thus obtained.

Moreover, it is known that 2-phenylethanol is a normal metabolite of fermentation by yeasts and that it is found at concentrations of from 10 to 35 mg/l in all fermented products. However, these concentrations are too low to justify the development of viable methods for extracting the 2-phenylethanol.

The subject of the invention is a new means of obtaining natural 2-phenylethanol. This new method consists in extracting 2-phenylethanol from distillation residues obtained during the production of alcohol by distillation.

Two differents techniques are used for production of alcohol by distillation: continuous distillation and the double heating technique in batch stills. All residues resulting from these techniques contain 2-phenylethanol with concentration that vary from 40 to 150 mg/l according to the type of raw material used for fermentation and the distillation technique.

In particular, residues from the first distillation in case of a double distillation in batch stills or residues from continuous distillation are characterized by concentration of 2-phenylethanol on the order of 40 to 70 mg/l. In these cases, the direct extraction of the molecule is difficult because of the large amount of suspended matter. Nevertheless because of their high pollutant charge, the residues are often concentrated by evaporation. Generated condensates do not contain suspended matter and are very low in dissolved solids. The concentration in 2-phenylethanol in condensates is similar to that of the residues before evaporation.

Advantageously, the method according to the invention is carried out for the extraction of 2-phenylethanol from the residues of the second distillation in the case of a double distillation in batch stills.

These residues are called "Spent Less" in the case of the manufacture of whisky and "Secondes de bonne chauffe" in the case of the manufacture of cognac. Indeed, 2-phenylethanol is found in non negligible amounts in these second distillation residues. As a guide 2-phenylethanol is present in Spent Lees at a concentration of from 100 to 150 mg/l.

Advantageously, the extraction of 2-phenylethanol from the distillation residues obtained during the production of alcohol is preceded by a step of clarification of the said residues. In fact, this clarification considerably facilitates the following step of extraction of the 2-phenylethanol because the residues contain suspended materials (20 to 250 mg/l) which tend to clog the membranes on account of their waxy consistency.

Even more advantageously, the residues are clarified by tangential microfiltration, which has the advantage of completely freeing the residues of the suspended particles. Furthermore, this technique has proven highly advantageous from an economic point of view.

Within the context of the present invention, the membranes used to carry out the tangential microfiltration are conventional mineral membranes.

Mineral membranes have the advantage of functioning efficiently at relatively high temperatures (50 to 60° C.), which makes it possible to obtain high permeate flow rates. Furthermore, the cleaning operations are thereby simplified.

The membranes used in the context of the invention are TECHSEP KERASEP™ membranes which have a cutoff threshold of $0.10\mu$ with internal channels 3.5 mm in diameter. The permeate flows obtained are between 200 and 600 $l/h/m^2$. However, the invention is not limited to this type of membrane in particular.

It is thus possible to clarify the second-distillation residues with a conversion factor of greater than 90%.

In a preferred method in accordance with the invention, 2-phenylethanol is extracted from the clarified residues by ion exchange using adsorbent resins. Within the context of the present invention, the resins used are adsorbent resins capable of binding lipophilic compounds. The best results were obtained with Dowex S 112 resins from the DOW company, but other resins may also be suitable.

The 2-phenylethanol thus adsorbed on the resin is then recovered in a conventional manner by elution from the column with an alcohol such as ethanol or another organic solvent.

In another preferred method in accordance with the invention, the 2-phenylethanol is extracted from the clarified residues by reverse osmosis. The reason for this is that it has been observed, unexpectedly, that this technique very efficiently allows the 2-phenylethanol to be retained by concentrating it with the aid of reverse osmosis membranes.

Since reverse osmosis gives rise to a retentate in which the 2-phenylethanol is retained and to a permeate consisting of everything which has not been retained, the retentate in effect undergoes a certain number of cycles of reverse osmosis, the effect of which is to concentrate it a little more on each cycle by elimination of water. In this way the retentate may be concentrated 100 fold by elimination of 99% of the water.

However, condensates resulting from the concentration by evaporation of residues from the first distillation in case of a double distillation in batch stills or residues from continuous distillation can be treated with the method according to the invention. Nevertheless, to reach a concentration of 2-phenylethanol of 10 g/l in the retentate produced by reverse osmosis the concentration factor must be higher than when treating residues of second distillation.

It should be emphasized that when tangential microfiltration is used to clarify the distillation residues, the subsequent reverse osmosis flow rates are thereby considerably improved.

The reverse osmosis membranes which can be used in the context of the present invention are membranes which have a porosity which is sufficiently low to be able to retain 2-phenylethanol. This is particularly the case for the reverse osmosis membranes conventionally used for the desalination of water. This is because this type of membrane is hydrophilic whereas 2-phenylethanol is hydrophobic; thus, the latter does not pass through the membrane. Examples of membranes which may be mentioned are the Filmtec membranes from the DOW company (reference BW-30-330)

whose level of retention of 2-phenylethanol remains greater than 98% irrespective of the operating conditions. However, other types of reverse osmosis membranes may also be suitable.

As regards the recovery of the 2-phenylethanol from the retentate obtained by reverse osmosis, this may be achieved conventionally by means of solvent-extraction followed by purification by distillation.

The invention is not limited to the present description and will be better understood with the aid of the examples which follow.

EXAMPLE 1

Extraction of 2-phenylethanol on an Adsorbent Column

A pilot test was performed on an adsorbent column 50 cm in height and 10 cm in diameter containing 4 l of Dowex S 112 resin.

250 l of Spent Lees were passed through this column at a flow rate ranging from 55 to 70 l/h.

The elution was performed with 10 l of 96% alcohol at a flow rate of 40 l/h, the eluate being fractioned into fractions of 1 l each. The 2-phenylethanol in each of the fractions is assayed by liquid phase chromatography. The results are collated in Table 1.

TABLE 1

| Fractions | 1 | 2 | 3 | 4 | 5 | 6 | 7 | 8 | 9 |
|---|---|---|---|---|---|---|---|---|---|
| 2-phenyl-ethanol in g/l | 0.013 | 0.25 | 23.81 | 24.18 | 11.13 | 5.31 | 2.106 | 0.1 | 0.47 |

Fractions 3, 4, 5, 6 and 7 were combined and then evaporated on a rotary evaporator under vacuum at 40° C. About 100 g of an aromatic oil containing 85% 2-phenylethanol were obtained. The 2-phenylethanol can then be purified by rectification.

GC/MS analysis of the crude oil obtained shows the presence, along with 2-phenylethanol, of many organic acids and sulphur-containing compounds.

EXAMPLE 2

Extraction of 2-phenylethanol by Reverse Osmosis 1650 l of Spent Lees, with a concentration of about 110 mg/l of 2-phenylethanol, were taken from an industrial still at the end of the second distillation. These Spent Lees were first treated by tangential microfiltration on a microfiltration pilot equipped with 0.25 $m^2$ of Techsep Kerasep™ membrane having a cutoff threshold of $0.10\mu$.

1500 l of clarified Spent Lees were obtained after 28 h of treatment.

These clarified Spent Lees were then concentrated by reverse osmosis on a pilot equipped with 2.5 $m^2$ of Filmtec BW 30-330 membranes.

After running for 16 hours, 17 l of retentate with a 2-phenylethanol content of 9.1 g/l and 1483 liters of a permeate with a 2-phenylethanol content of 4.1 mg/l were obtained.

We claim:

1. Method for extracting 2-phenylethanol, in which the 2-phenylethanol is extracted from the distillation residues obtained during the production of alcohol.

2. Method for extracting 2-phenylethanol according to claim 1, in which the 2-phenylethanol is extracted from the second-distillation residues obtained during the production of alcohol by double-distillation.

3. Method for extracting 2-phenylethanol according to claim 1 or 2, in which extraction of the 2-phenylethanol is preceded by a step of clarification of the residues.

4. Method for extracting 2-phenylethanol according to claim 3, in which the residues are clarified by tangential microfiltration.

5. Method for extracting 2-phenylethanol according to claim 3, in which the 2-phenylethanol is then recovered by elution of the column with an alcohol or any other organic solvent.

6. Method for extracting 2-phenylethanol according to claim 5, in which the 2-phenylethanol is then recovered by elution of the column with an alcohol or any other organic solvent.

7. Method for extracting 2-phenylethanol according to claim 3, in which the 2-phenylethanol is extracted by reverse osmosis.

8. Method for extracting 2-phenylethanol according to claim 7, in which the 2-phenylethanol contained in the retentate obtained by reverse osmosis is then recovered using a solvent.

* * * * *

UNITED STATES PATENT AND TRADEMARK OFFICE
CERTIFICATE OF CORRECTION

PATENT NO. : 5,965,780
DATED : October 12, 1999
INVENTOR(S) : Savina et al.

It is certified that error appears in the above-identified patent and that said Letters Patent is hereby corrected as shown below:

Column 1, line 53, delete "Spent Less" and insert -- Spent Lees -- .

Signed and Sealed this

Twenty-second Day of May, 2001

*Attest:*

NICHOLAS P. GODICI

*Attesting Officer*  *Acting Director of the United States Patent and Trademark Office*